(12) United States Patent
Chen

(10) Patent No.: US 7,862,801 B2
(45) Date of Patent: *Jan. 4, 2011

(54) ADHESIVE DENTAL BLEACHING COMPOSITIONS COMPRISING POLYVINYLPYRROLIDONE

(75) Inventor: Tianming Chen, Qinhuangdao (CN)

(73) Assignee: Ultradent Products, Inc., South Jordan, UT (US)

( * ) Notice: Subject to any disclaimer, the term of this patent is extended or adjusted under 35 U.S.C. 154(b) by 1 day.

This patent is subject to a terminal disclaimer.

(21) Appl. No.: 10/870,293

(22) Filed: Jun. 17, 2004

(65) Prior Publication Data

US 2004/0223923 A1 Nov. 11, 2004

Related U.S. Application Data

(63) Continuation of application No. 10/715,003, filed on Nov. 17, 2003, now Pat. No. 7,128,899, which is a continuation of application No. 10/288,239, filed on Nov. 5, 2002, now Pat. No. 6,730,316, which is a continuation-in-part of application No. 09/770,489, filed on Jan. 27, 2001, now Pat. No. 6,500,408.

(51) Int. Cl.
*A61Q 11/00* (2006.01)
*A61K 8/00* (2006.01)
*A61K 8/22* (2006.01)
*A61C 3/00* (2006.01)

(52) U.S. Cl. .................. 424/53; 424/49; 424/401; 424/435; 424/443; 424/448; 424/449; 433/216; 433/217.1

(58) Field of Classification Search .............. 424/53, 424/448, 449
See application file for complete search history.

(56) References Cited

U.S. PATENT DOCUMENTS

| | | | |
|---|---|---|---|
| 3,499,844 A | 3/1970 | Kibbel et al. | |
| 3,657,413 A | 4/1972 | Rosenthal | |
| 3,996,152 A | 12/1976 | Edwards et al. | |
| 4,412,028 A * | 10/1983 | Lundberg et al. | 524/364 |
| 4,514,384 A * | 4/1985 | Gallina | 514/179 |
| 4,775,525 A | 10/1988 | Pera | |
| 4,900,721 A | 2/1990 | Bansemir | |
| 4,983,380 A | 1/1991 | Yarborough | |
| 5,000,942 A | 3/1991 | Libin | |
| 5,008,093 A | 4/1991 | Merianos | |
| 5,008,106 A | 4/1991 | Merianos et al. | |
| 5,009,885 A | 4/1991 | Yarborough | |
| 5,098,303 A | 3/1992 | Fischer | |
| 5,108,742 A | 4/1992 | Merianos | |
| 5,122,365 A | 6/1992 | Murayama | |
| 5,130,124 A * | 7/1992 | Merianos et al. | 424/53 |
| 5,177,113 A * | 1/1993 | Biss et al. | 514/772.5 |
| 5,183,901 A | 2/1993 | Login et al. | |
| RE34,196 E | 3/1993 | Munro | |
| 5,206,385 A | 4/1993 | Login et al. | |
| 5,234,342 A | 8/1993 | Fischer | |
| 5,236,696 A | 8/1993 | Catiis et al. | |
| 5,256,328 A | 10/1993 | Cavanagh et al. | |
| 5,312,619 A * | 5/1994 | Shih et al. | 424/78.25 |
| 5,376,006 A * | 12/1994 | Fischer | 433/215 |
| 5,401,495 A | 3/1995 | Murayama | |
| 5,409,631 A | 4/1995 | Fischer | |
| 5,571,501 A | 11/1996 | Toy | |
| 5,573,399 A | 11/1996 | McClintock, II | |
| 5,575,654 A | 11/1996 | Fontenot | |
| 5,599,525 A | 2/1997 | Hsu et al. | |
| 5,645,428 A | 7/1997 | Yarborough | |
| 5,648,064 A | 7/1997 | Gaffar et al. | |
| 5,670,138 A * | 9/1997 | Venema et al. | 424/52 |
| 5,685,712 A | 11/1997 | Fischer | |
| 5,692,900 A | 12/1997 | Fischer | |
| 5,698,182 A | 12/1997 | Prencipe et al. | |
| 5,713,738 A | 2/1998 | Yarborough | |
| 5,722,833 A | 3/1998 | Fischer et al. | |
| 5,725,843 A | 3/1998 | Fischer | |
| 5,736,158 A | 4/1998 | Quast | |
| 5,746,598 A | 5/1998 | Fischer | |
| 5,747,008 A | 5/1998 | Wason et al. | |

(Continued)

FOREIGN PATENT DOCUMENTS

| WO | WO 99/12517 | 3/1999 |
|---|---|---|
| WO | WO 00/54699 | 3/2000 |

OTHER PUBLICATIONS

PVP, http://online1.ispcorp.com/Brochures/Performance%20Chemicals/PVP.pdf, pp. 1-14, retrieved Dec. 2009.*
Reisch, Marc, Chemical & Engineering News, vol. 80, No. 28, p. 11, Jul. 2002.*
Email from Dan Fischer to Dan McCarthy and Micha Barach dated Apr. 8, 2003 and confirming that "PVP below 25% by weight is clearly in the prior art".
Office Action dated Oct. 2, 2001 cited in U.S. Appl. No. 09/770,489.
Notice of Allowance dated Aug. 26, 2002 cited in U.S. Appl. No. 09/770,489.
Office Action dated Jun. 25, 2003 cited in U.S. Appl. No. 10/288,239.
Notice of Allowance dated Dec. 30, 2003 cited in U.S. Appl. No. 10/288,239.

(Continued)

*Primary Examiner*—Frederick Krass
*Assistant Examiner*—Lezah W Roberts
(74) *Attorney, Agent, or Firm*—Workman Nydegger

(57) ABSTRACT

A dental bleaching composition comprises a dental bleaching agent and a polyvinylpyrrolidone thickening agent. The bleaching composition may include water, flavoring agents, a basic substance and desensitizing agents, as desired. Polyvinylpyrrolidone avoids acid etching and chelation of teeth that were problematic in bleaches using carbomer as a thickener. A delivery system for delivering the bleaching composition comprises the aforementioned dental bleaching composition in combination with a moisture-resistant barrier layer such as a dental tray or a flexible strip of material.

27 Claims, 8 Drawing Sheets

U.S. PATENT DOCUMENTS

| | | |
|---|---|---|
| 5,759,037 A | 6/1998 | Fischer |
| 5,759,038 A | 6/1998 | Fischer |
| 5,759,598 A | 6/1998 | Gaier |
| 5,760,102 A * | 6/1998 | Hall et al. .................. 523/120 |
| 5,766,011 A | 6/1998 | Sibner |
| 5,766,574 A | 6/1998 | Christina-Beck et al. |
| 5,770,105 A | 6/1998 | Fischer |
| 5,770,182 A | 6/1998 | Fischer |
| 5,785,527 A | 7/1998 | Jensen et al. |
| 5,785,957 A | 7/1998 | Losee et al. |
| 5,846,058 A | 12/1998 | Fischer |
| 5,851,512 A | 12/1998 | Fischer |
| 5,855,870 A | 1/1999 | Fischer |
| 5,858,332 A | 1/1999 | Jensen et al. |
| 5,879,691 A | 3/1999 | Sagel et al. |
| 5,891,453 A * | 4/1999 | Sagel et al. ................. 424/401 |
| 5,894,017 A | 4/1999 | Sagel et al. |
| 5,922,307 A | 7/1999 | Montgomery |
| 5,928,628 A | 7/1999 | Pellico |
| 5,944,528 A | 8/1999 | Montgomery |
| 5,944,698 A | 8/1999 | Fischer et al. |
| 5,945,032 A | 8/1999 | Breitenbach et al. |
| 5,985,249 A | 11/1999 | Fischer |
| 5,989,526 A | 11/1999 | Aaslyng et al. |
| 5,989,569 A | 11/1999 | Dirksing et al. |
| 6,010,683 A | 1/2000 | Fischer |
| 6,036,493 A | 3/2000 | Sharma |
| 6,036,943 A | 3/2000 | Fischer |
| 6,045,811 A | 4/2000 | Dirksing et al. |
| 6,080,397 A | 6/2000 | Pfirrmann |
| 6,086,372 A | 7/2000 | Diamond |
| 6,086,855 A | 7/2000 | Fischer |
| 6,089,869 A | 7/2000 | Schwartz |
| 6,096,328 A | 8/2000 | Sagel et al. |
| 6,108,850 A | 8/2000 | McLaughlin |
| 6,116,900 A | 9/2000 | Ostler |
| 6,136,297 A | 10/2000 | Sagel et al. |
| 6,149,211 A | 11/2000 | Losee et al. |
| 6,162,055 A | 12/2000 | Montgomery et al. |
| 6,183,251 B1 | 2/2001 | Fischer |
| 6,193,958 B1 | 2/2001 | Edwards et al. |
| 6,221,341 B1 | 4/2001 | Montgomery |
| 6,239,090 B1 * | 5/2001 | Marquis et al. ............. 510/201 |
| 6,306,370 B1 | 10/2001 | Jensen et al. |
| 6,309,625 B1 | 10/2001 | Jensen et al. |
| 6,312,671 B1 | 11/2001 | Jensen et al. |
| 6,322,774 B1 | 11/2001 | Jensen et al. |
| 6,368,576 B1 | 4/2002 | Jensen et al. |
| 6,387,353 B1 | 5/2002 | Jensen et al. |
| 6,409,993 B1 | 6/2002 | Jensen et al. |
| 6,419,905 B1 | 7/2002 | Alvarez Hernandez |
| 6,500,408 B2 | 12/2002 | Chen |
| 6,503,485 B1 | 1/2003 | Allred |
| 6,545,147 B1 | 4/2003 | Seebach et al. |
| 6,545,174 B2 | 4/2003 | Habeck et al. |
| 6,545,283 B1 | 4/2003 | Williams et al. |
| 6,548,470 B1 | 4/2003 | De Buzzaccarini et al. |
| 6,551,579 B2 | 4/2003 | Sagel et al. |
| 6,582,708 B1 | 6/2003 | Sagel et al. |
| 6,682,721 B2 | 1/2004 | Kim et al. |
| 6,689,344 B2 | 2/2004 | Chang et al. |
| 2001/0021374 A1 * | 9/2001 | Montgomery ................ 424/53 |
| 2003/0082114 A1 | 5/2003 | Kim et al. |

OTHER PUBLICATIONS

Office Action dated Nov. 30, 2005 cited in U.S. Appl. No. 10/715,003.

Notice of Allowance dated Jun. 1, 2006 cited in U.S. Appl. No. 10/715,003.

Dentistry Today Buyers' Guide to Whitening Systems, Par5126B0B2133, Doc 1997.

Bitter, Norman C., "A scanning electron microscope study of the long-term effect of bleaching agents on the enamel surface in vivo", General Dentistry (Jan./Feb. 1998), pp. 84-88.

Shannon, Heather et al., "Characterization of enamel exposed to 10% carbamide peroxide bleaching agents", Quintessence International (vol. 24, No. 1, 1993), pp. 39-44.

Perdigao, Jorge et al., "Ultra-morphological study of the interaction of dental adhesives with carbamide peroxide-bleached enamel", American Journal of Dentistry (vol. 11, No. 6, Dec. 1998), pp. 291-301.

Pinheirojunior, Elilton Cavalcante et al., "In Vitro Action of Various Carbamide Peroxide Gel Bleaching Agents on the Microhardness of Human Enamel", Braz. Dent. J. (1996) 7(2): 75-79.

"Buyers' Guide to Whitening System", Dentistry Today (Dec. 2000), pp. 90, 92, 94, 96, 98, 100, 101 & 102.

Denmat Website (http://www.denmat.com), "Professional Tooth Whitening Systems" (2 pages, Jan. 2001).

Discus Dental Website (http://www.discusdental.com), "Whitening" (7 pages, Jan. 2001).

Ultradent Website (http://www.ultradent.com), "Materials & Procedures Manual—Tooth Whitening" (9 pages, Jan. 2001).

* cited by examiner

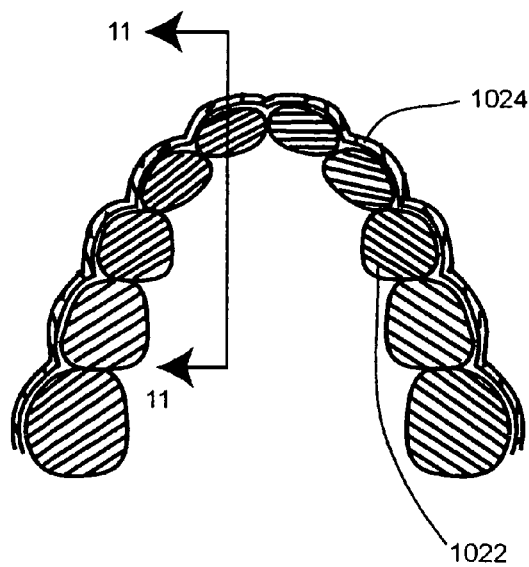
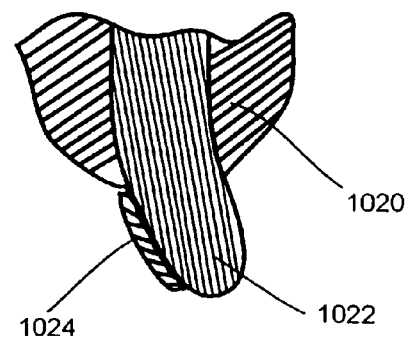
Fig.10    Fig.11
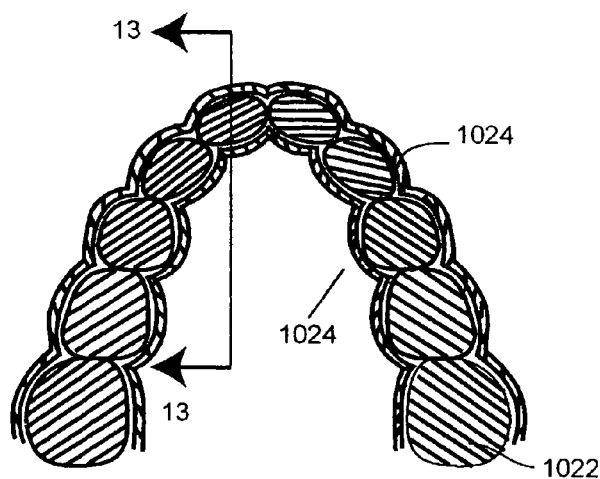
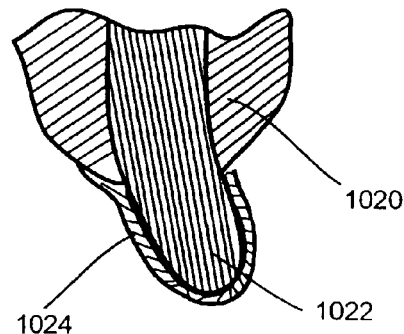
Fig.12    Fig.13

ADHESIVE DENTAL BLEACHING COMPOSITIONS COMPRISING POLYVINYLPYRROLIDONE

CROSS-REFERENCE TO RELATED APPLICATIONS

This application is a continuation of U.S. application Ser. No. 10/715,003, filed Nov. 17, 2003, now U.S. Pat. No. 7,128, 899 which is a continuation of U.S. application Ser. No. 10/288,239, filed Nov. 5, 2002, now U.S. Pat. No. 6,730,316, which is a continuation-in-part of U.S. application Ser. No. 09/770,489, filed Jan. 27, 2001, now U.S. Pat. No. 6,500,408. U.S. Pat. No. 6,730,316 and copending U.S. Ser. No. 10/715, 003 are incorporated herein in their entirety.

BACKGROUND OF THE INVENTION

1. The Field of the Invention

Dental bleaching and dental bleaches are disclosed. Discussion is provided concerning viscous dental bleaches which may be placed into a tray or otherwise held against a patient's teeth in order to cause a lightening, whitening and stain removal effect without damaging the enamel of the patient's teeth.

2. The Relevant Technology

The ability to whiten both vital and non-vital teeth with peroxides has been known for well over 40 years. By nature, the human race is very diversified genetically as to tooth shape and color. The color of teeth within the human race usually ranges from whites, blacks, greys, browns and yellows. Environment, nutrition, medication and diet can affect tooth color. Some foods such as blueberries, cranberries, coffee and tea can significantly alter a person's tooth color from its original state. Other habits like smoking or chewing of tobacco can darken a person's teeth over a period of time. Tetracycline and other medications can have a darkening or graying effect on teeth. Children born to women who ingested tetracycline during pregnancy often have permanently stained teeth. Tetracycline staining may come in definite unsightly bands on the teeth.

A desire among the populace for bright white teeth has increased as economic stature and standards of living have improved. In developing and developed nations, social standing, personal relations and career opportunities can be positively or negatively influenced by the appearance of one's teeth. Generally, it is preferred to have white teeth rather than to have dark teeth. Since whiter teeth are generally more desirable, many materials have been devised to whiten an individual's teeth by chemical means.

The most commonly accepted chemicals used in teeth whitening today are peroxides. Peroxides are known in the art as oxidizing agents and are highly reactive. Organic molecules that reflect specific wavelengths of light back to our eyes are usually very complex molecules. These colorful substances are usually called dyes and pigments. Oxidation of these organic dyes and pigments usually destroys their ability to absorb light and therefore renders them white. For example, the paper industry uses hydrogen peroxide to bleach brown wood pulp to white wood pulp.

Peroxides are a safe teeth whitener, because they are generally deemed safe from a physiological standpoint as compared to other oxidizing agents. The peroxides of choice for teeth whitening are: hydrogen peroxide, carbamide peroxide, sodium perborate, and sodium percarbonate. When these peroxides are in appropriate contact with teeth they will usually oxidize both internal and external organic stains, rendering the teeth whiter. In contrast, inorganic stains are usually not affected by peroxides. Individuals with predisposed inorganic stains usually will not experience a whitening effect with the application of peroxides. However, the majority of the world's human population will experience a whitening effect through the application of peroxides to teeth.

Since the use of peroxides has been generally accepted for use in teeth whitening, a multitude of methods for applying peroxides have been devised. One method of application is to paint a peroxide in water solution directly on the teeth. A problem with water solutions of peroxides is that they are too thin or runny. This causes them to run off of the teeth due to the force of gravity and run onto the soft tissues of the mouth. High concentrations of peroxides are painfully irritating to soft tissue, causing serious discomfort to a patient. The method of painting a water solution of peroxide on a person's teeth is usually an "in-office" procedure, because of the inherent difficulties associated with patients applying it to their own teeth. In most cases, the patient's lips are painfully retracted during the entire treatment, and the patient is confined to sitting in the dental chair. The danger of the peroxide solution running off the teeth and contacting soft tissue is always present when peroxide and water bleaching solutions are used.

Patient comfort during the bleaching treatment may be improved by shortening the time of bleaching. In general there are three ways to bleach teeth faster. The first is to increase the concentration of the peroxide. The second is to increase the pH of the peroxide with a basic substance. Basic substances such as sodium hydroxide will destabilize peroxide solutions, therefore making the peroxide more reactive so that it carries out its whitening effect more quickly. The third way to bleach teeth more quickly is to speed up the reaction process by heating the peroxide solution. Heat accelerates almost all chemical reactions, including bleaching. In order to reduce bleaching treatment time, any one or combination of the above methods can be implemented or augmented.

There are physiological problems associated with speeding up the bleaching process, however. First, as peroxide concentration in the bleach is increased, the bleach is more irritating to soft tissues. Second, as the pH level is increased in the bleach, the bleach becomes more caustic to soft tissue. Third, as temperature of the bleach is increased, the bleaching process is more likely to burn soft tissue or even kill teeth.

The runniness of aqueous peroxide solutions and the problems associated with accelerating the bleaching process incentivized the dental care provider to isolate soft tissues from the dental bleach. This can be accomplished by methods known in the dental profession such as use of a rubber dam. First, the patient's lips are painfully retracted, followed by placing a pre-punched rubber sheet or dam over each individual tooth. Placing a rubber dam on each tooth is slow and does not guarantee a perfect seal against leakage of the peroxide solution onto soft tissue. In order to satisfy patient demand for rapid and complete bleaching of teeth, the dental practitioner must increase risk to the patient by use of more concentrated bleaches. In order to treat teeth with a bleach that would essentially be non-irritating to soft tissues would take 2-5 full days of bleaching to see significant improvement in whitening. A patient would be very uncomfortable sitting in a dental chair with their cheeks retracted for that period of time, and the cost of such treatment would be prohibitive.

Recognition of these inherent problems associated with the "paint-on" method of bleaching with aqueous peroxides brought about significant improvements in the art of tooth bleaching. The improvements came by adding viscosity-building chemicals to the peroxide solutions. By increasing the viscosity of bleaching solutions, the ability of the bleach to flow, run or drip decreased. Substances such as glycerin, high molecular weight polyethylene glycol, fumed silica, high molecular weight polypropylene glycol, xanthan gum, hydroxy propyl cellulose and carbomer (marketed under the trade name CARBOPOL®), have generally been used to increase the viscosity of peroxide solutions.

In order to also reduce the detrimental effects of bleaching gels coming into contact with soft tissues, the pH of the peroxide solution was adjusted to around pH=7. When the concentration of peroxide was reduced, patients were required to keep the bleaching gel in contact with their teeth for a longer period of time in order to achieve the desired whitening result. This consideration was addressed by use of a dental tray which holds the bleach in contact with teeth, but which prevents the bleach from flowing away from the teeth to contact soft tissues. Use of a dental tray permits the bleach to remain in intimate contact with teeth for long periods of time without requiring the patient to sit in a dental chair with retracted cheeks. When a dental tray is used to accommodate long periods of exposure of bleach to teeth, lower concentrations of peroxides in bleach may also be used, therefore reducing the risk to soft tissue. A dental tray is an arch-shaped container which holds the bleaching material against the teeth. The dental tray also acts as a barrier against dilution of the bleach by saliva and the eventual swallowing of the bleaching material in a short period of time.

The viscosity-building material used in almost all bleaching gels today is carbomer (CARBOPOL®), manufactured by B.F. Goodrich. CARBOPOL® is a modified polyacrylic acid hydrophilic polymer, capable of forming viscous gels at concentrations above as little as 5% by weight. CARBOPOL® is the material of choice for current bleach manufacturers because it thickens peroxide solutions to a point where they will not run out of a dental tray or away from the teeth to soft tissue areas. This allows the bleach to stay in contact with the teeth for extended periods of time and protects soft tissues. The use of a dental tray and a viscous bleach allows a low concentration bleach to effectively whiten a person's teeth over a 1-2 week period of time with minimal risk to the patient. CARBOPOL® is generally the only material of choice that delivers the required high viscosity properties for a 4-8 hour bleaching period.

Fumed silica is an alternative thickening agent, but it is considered a poor choice for use in dentistry. Fumed silica is not soluble in peroxide solutions; therefore, it only suspends in the solution. At higher loadings of silica, peroxide solutions turn into a putty instead of a viscous gel. A putty suffers from not being able to flow freely around the teeth to adequately bleach them. Silica also absorbs peroxide solutions, thus binding the peroxide so that it is not as available for bleaching. Silica can also act disadvantageously as a wick to peroxide solutions. Silica-thickened bleaches dry up very quickly when placed on the teeth, and it is well known that dry peroxides do not bleach as effectively as aqueous peroxides. It is therefore generally concluded that silica is a poor choice as a thickener for tray bleaching.

There are other natural gums that could also be considered as a thickener for tray bleaching. Materials such as xanthan gum, pectin, guar gum and hydroxy propyl cellulose have been considered in the past. Natural gums are also poor materials of choice for use as thickeners in dental bleaching, although they are used widely in the food industry as thickeners. Natural gums at low concentrations are adequate for thickening bleaches that are still runny and able to drip when poured. Natural gums at high concentrations tend to turn into gelatinous masses. Gelatin does not flow and tends to clump together, thus limiting its ability to adequately flow around the teeth to effectively bleach. For this reason it is not used as the sole thickener in viscous bleaches. It has generally been concluded by the industry that natural gums are not desirable for use in tray bleaching.

Other thickening agents used in the dental industry are high molecular weight water soluble waxes, such as polyethylene glycol and polypropylene glycol. Water soluble waxes are not used as the sole thickener for peroxide solutions, however, because they do not thicken adequately. At high loadings of water soluble waxes, bleaches are still runny and maintain no gel-type properties. Bleaches made from water soluble waxes are not highly viscous and can easily escape out of the tray. It is generally known that water soluble waxes used to thicken peroxide solutions are not desirable for tray bleaching.

Considering the shortcomings of the various thickeners, CARBOPOL® remains the best compromise as a thickener for tray bleaching. CARBOPOL® has more or less the desired thickening properties to deliver a viscous bleaching gel. For this reason it is widely used as the thickener of choice in almost all currently marketed available tray bleaching materials.

CARBOPOL®, though popular, has shortcomings as well. CARBOPOL® is a cross-linked polyacrylic acid. A polyacrylic acid has the structure —$CH_2CH(CO_2H)$—. When CARBOPOL® is dispersed in water, the resulting mixture becomes acidic. Acidic substances have the ability to remove cations from inorganic matrixes to form a salt. The enamel that covers the outer portion of human teeth is composed of calcium hydroxyl apatite. Calcium hydroxyl apatite is a crystalline material similar to bone ceramic. Acidic substances like vinegar or lemons can remove enamel by forming a salt with the calcium in our enamel. It is well known in the dental industry that individuals who suck on lemons can literally etch large portions of enamel off their teeth.

Similarly, CARBOPOL® is a long chain of repeating acids, and when dispersed in an aqueous solution, it can acidically remove calcium from teeth and therefore remove tooth enamel. Since CARBOPOL® bleaches are intended for long-term bleaching regimes, keeping the bleach in contact with the tooth for more than just a few minutes, they may remove enamel during these extended bleaching sessions. It is accepted in the dental industry that the removal of layers of enamel is harmful to an individual's dental health and can lead to mottling (wearing away) of the teeth.

Manufacturers of dental bleach containing CARBOPOL® use bases to raise the pH of the bleaching material. The bases of choice generally have been sodium hydroxide, potassium hydroxide and triethanolamine. Bases are used to raise the pH of the dental bleach to less acidic levels to reduce removal of enamel by acidic etching. Since CARBOPOL® is known to be more stable in acidic ranges, almost all manufacturers of tray bleaching systems adjust their CARBOPOL® bleaches to a pH range of 5.5-6.5. The lower the pH of the bleach, the more enamel is removed by acidic etching. Long-term bleaching only lengthens out the acidic etching process. Even a bleach pH of 6.0 can remove tooth enamel during bleaching.

Additionally, it is difficult to achieve consistent pH from batch to batch of dental bleach. Because of the variations in the average molecular weight of CARBOPOL®, specially tailored quantities of base must be added to separate batches to attain a constant pH level in the dental bleach product. But it is a common practice for manufacturers to add a standard amount of base to each batch of bleach, resulting in pH variability from batch to batch. This variability will always exist even if the manufacturer intends his bleach to be at pH 7.

Another problem in using CARBOPOL® is that it has long chains of polyacrylic acid that sometimes fold around themselves to form a ball. When this happens, the inner protected parts of the CARBOPOL® chain wet at a much slower rate than the outer parts of the chain. This means that the pH of the CARBOPOL® and hence the dental bleach will vary with the total wetting time. Consequently, CARBOPOL® bleaches may have a different pH at one week after manufacture than on the day of manufacture. The only way to rectify this problem is for the dental bleach manufacturer to keep the CARBOPOL® bleach in storage for a period of time to allow pH stabilization, followed by a final pH adjustment. Such a practice is not economical. All these factors make it extremely difficult to manufacture CARBOPOL® dental bleach that has a consistent pH level both from batch to batch and over time.

Acidic etching, as explained above, is not the only cause of calcium being removed from tooth enamel. Organic acids can also remove cations by the process of chelation. Carboxylic acids have an affinity to form a salt with cations. This affinity for cations varies by the type of cations. For example, a carboxylic acid can form a salt with an element in the alkaline family, such as lithium, sodium, or potassium. The affinity to form an ionoic bond with an alkaline element is moderate. This we know because most organic acid-alkaline salts will ionize (dissolve) in water. However, the affinity of a carboxylic acid to an alkaline earth element such as beryllium, magnesium or calcium is much stronger. The affinity of an alkaline earth element to an organic acid is very strong, because most organic acid-alkaline earth salts do not readily ionize in water. Organic acids therefore have a higher affinity to bind with calcium than they do to sodium or potassium. This same principle is used during crown cementation with glass ionomer cements. Crown cementation is achieved because the polyacrylic acid (whether neutralized or un-neutralized) reacts with the alkaline earth cations of the ion leaching glass. Thus, organic acids, initially neutralized with sodium hydroxide to form a sodium salt, would switch to a calcium salt if calcium hydroxide were added to the mixture.

CARBOPOL® dispersed into water cannot be neutralized by calcium hydroxide without precipitating the polymer. Therefore, there are no CARBOPOL® bleaches neutralized with calcium hydroxide. Almost all CARBOPOL® bleaches are pH adjusted with sodium or potassium hydroxide.

There is a constant battle going on between the alkaline salts of CARBOPOL® and the calcium of the enamel. The carboxylic acid-alkaline salts of the CARBOPOL® have a higher binding power for the calcium of the enamel. Therefore, through the process of chelation, calcium is constantly being removed from the tooth enamel by CARBOPOL®-based bleaches.

Although CARBOPOL® is very effective in creating viscous gels for tray bleaching of teeth, its side effects in acid etching of tooth enamel and chelation are damaging to the very teeth that it is desired to restore to a more aesthetic condition. Information concerning the detrimental effects of prior art dental bleaches on tooth enamel can be found in the following articles: (i) Perdigao, J., et al., "Ultra-Morphological Study of the Interaction of Dental Adhesives with Carbamide Peroxide-Bleached Enamel", *American Journal of Dentistry*, vol. II, No. 6, pp. 291-301, December 1998; (ii) Pinheirojunior, E. C., et al., "In Vitro Action of Various Carbamide Peroxide Gel Bleaching Agents on the Microhardness of Human Enamel", *Braz. Dent. J.*, 7(2): 75-79 (1996); (iii) Shannon, et al., "Characterization of Enamel Exposed to 10% Carbamide Peroxide Bleaching Agents", *Quintessence International*, vol. 24, no. 1, pp. 39-44 (1993); (iv) Bitter, N., "A Scanning Electron Microscope Study of the Long-Term Effect of Bleaching Agents on the Enamel Surface In Vivo", *General Dentistry*, pp. 84-88, (January-February 1998). The prior art shows a need for dental bleach and a method for its use that includes a thickener or gelling agent that does not attack or react with tooth enamel.

SUMMARY OF THE INVENTION

Improved dental bleaches are disclosed. Some of the embodiments include bleaches that do not attack or react with tooth enamel. The dental bleaches have a tendency to lighten, whiten and remove stains and oxidize complex organic molecules from the teeth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 10 is a cross-sectional view showing adjacent teeth having the strip of material conforming thereto and adhesively attached to the teeth by means of a substance located between the teeth and the strip of material.

FIG. 11 is a cross-sectional elevation view of a tooth and adjoining soft tissue, taken along section line 11-11 of FIG. 10, disclosing the strip conforming to and adhesively attached to the tooth by means of the substance located between the tooth and the strip of material.

FIG. 12 is a cross-sectional view, similar to FIG. 10, showing a strip of material conforming to the teeth and the adjoining soft tissue and adhesively attached to both sides of the teeth by means of the substance located between the teeth and the strip of material.

FIG. 13 is a cross-sectional elevation view, taken along section line 13-13 of FIG. 12, showing the strip of material conforming to both the tooth and the adjoining soft tissue and adhesively attached to both sides of the tooth by means of the substance located between the tooth and the strip of material.

DETAILED DESCRIPTION OF THE PREFERRED EMBODIMENTS

A. Materials for Use in Dental Bleach

A dental bleach may have several components including a bleaching agent, a basic agent, a thickening agent, a flavoring agent, a desensitizing agent, and others, or a subset thereof.

1. Bleaching Agent

Suitable bleaching agents will include any material capable of releasing an oxidizing agent such as free radical oxygen ions for contacting teeth and removing stains therefrom via an oxidation process. Most common bleaching agents at this time are peroxides, including but not limited to hydrogen peroxide, carbamide peroxide, sodium perborate, and sodium percarbonate. Other peroxides and other oxidizing agents and bleaching agents may be utilized in addition to or in substitution of these materials.

2. Thickening Agent

Figure 1:
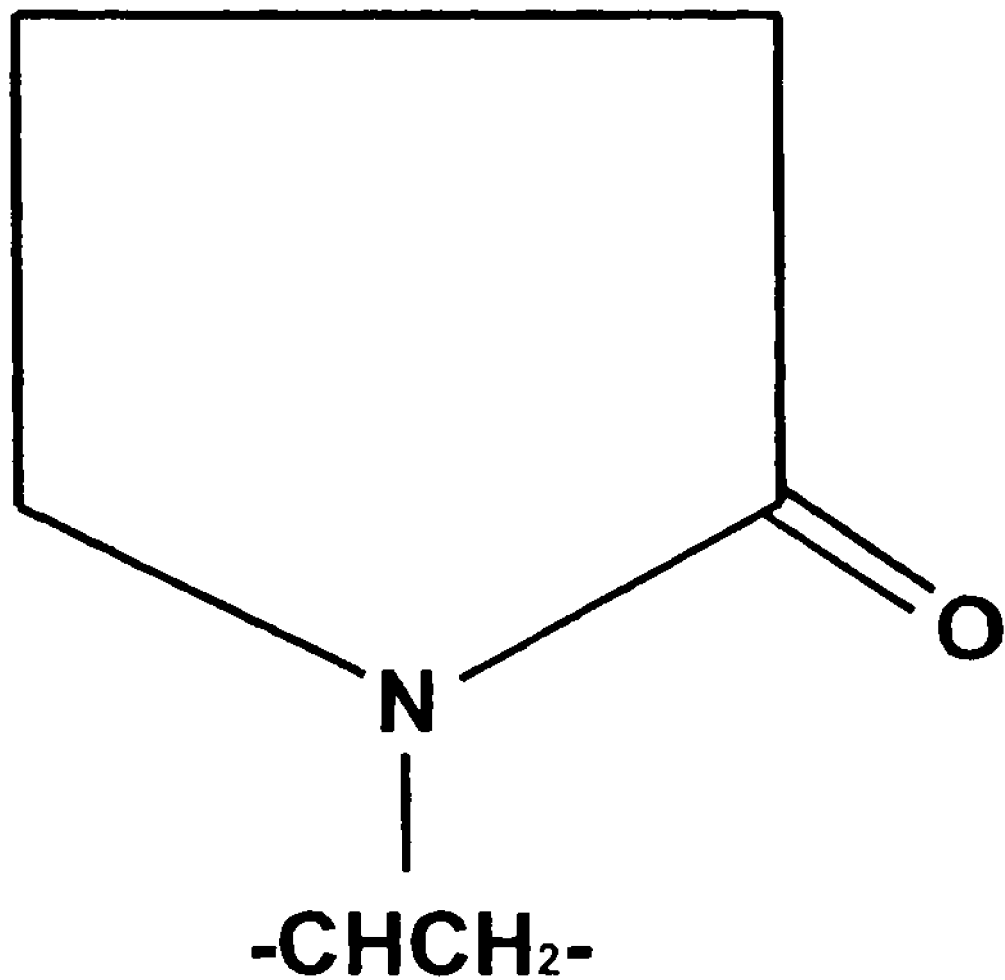
FIG. 1 depicts the chemical structure of polyvinyl pyrrolidone.

Dental bleaches can include a thickening agent in order to avoid runoff of the dental bleach and consequent contact with sensitive soft tissues, and in order to keep the bleach in contact with teeth. A suitable thickening agent will serve to increase viscosity of the dental bleach while avoiding substantial interference with the release of oxygen ions from the bleaching agent or the contact of those oxygen ions with teeth to be bleached. In some embodiments, the thickening agent used will include polyvinylpyrrolidone. FIG. 1 depicts the chemical structure of polyvinylpyrrolidone. Polyvinylpyrrolidone is also referred to as "povidone".

Polyvinylpyrrolidone has the advantage of serving as a thickening agent or gelling agent while failing to: (i) interfere with release of oxygen ions from the bleaching agent or contact of those oxygen ions to the teeth to bleached, (ii) chemically etch tooth enamel, (iii) remove calcium from tooth enamel by chelation, and (iv) solidify the dental bleach.

Polyvinylpyrrolidone is a tertiary amide based polymer. It contains no organic acid in its structure and therefore cannot acid etch or chelate teeth. Polyvinylpyrrolidone based bleaches are enamel safe and therefore will present a significant improvement over the prior art. Polyvinylpyrrolidone is easily dispersed into water to make highly viscous gels for tray bleaching at around 5-40% by weight. Polyvinylpyrrolidone may also be considered a tackifying agent because the increased viscosity of dental bleach that it produces has a sticky or tacky feel enabling it to adhere to teeth for the time required to carry out the bleaching process.

The most desirable molecular weights for the thickener used in the bleach is from about 90,000-1,500,000. Molecular weight may be determined by light scattering methods, size exclusion chromatography and other methods. Thickeners with a molecular weight outside that range can be used as well, as illustrated by the examples. As a general rule, the lower the molecular weight of the polyvinylpyrrolidone used, the more polyvinylpyrrolidone that is required to achieve the desired thickening.

3. Liquid Component

In its raw form, polyvinylpyrrolidone is a white powder. In order to form a gel useful in a dental bleach, a liquid component must be added to it. In some embodiments, suitable liquid components of the gel include water, glycerin, propylene glycol, liquid polyethylene glycol, liquid polypropylene glycol, ethanol, and other suitable liquid components. Any of the liquid components can be used singly or in combination.

4. Basic Substance

Figure 4:
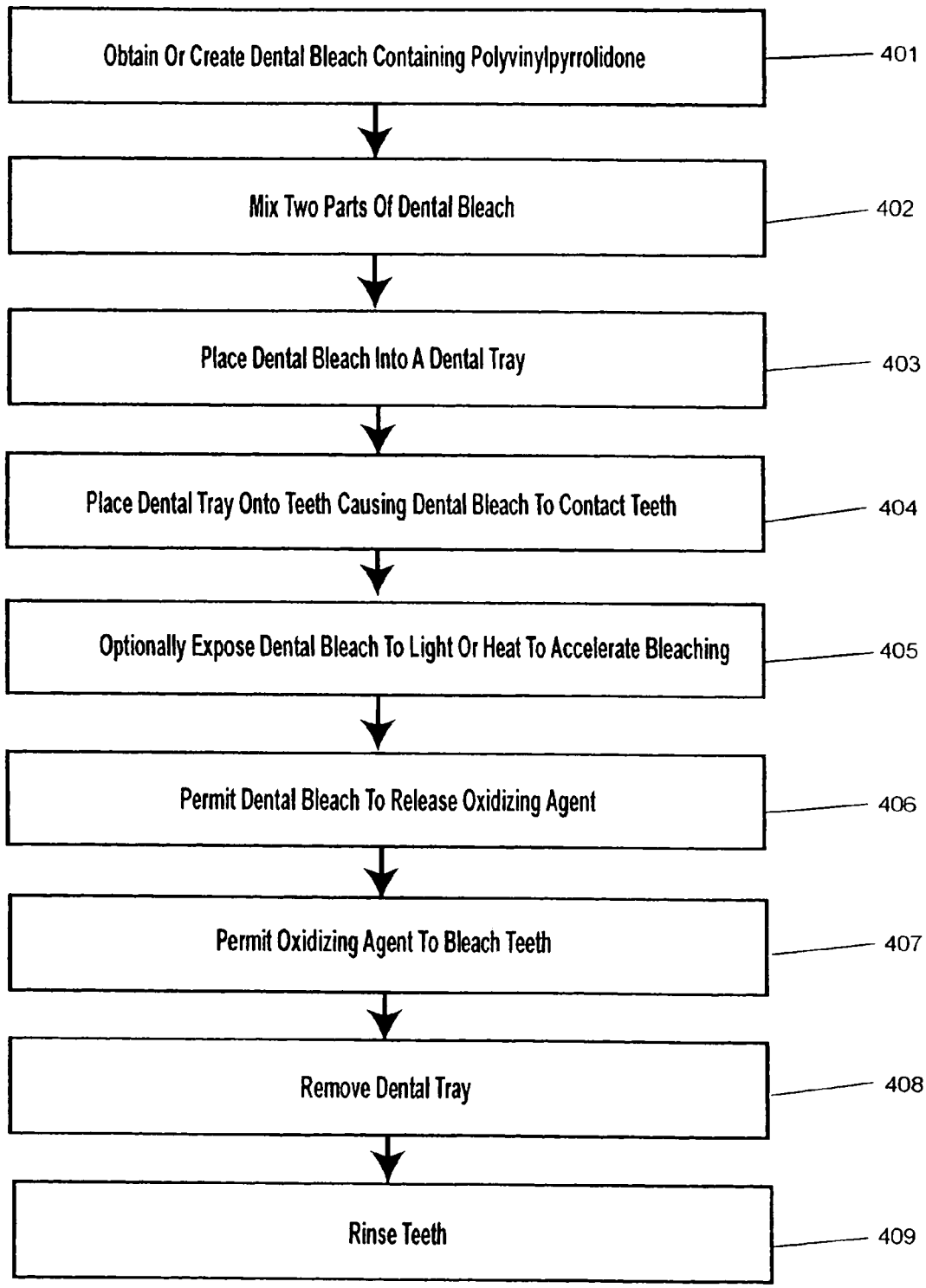
FIG. 4 depicts a series of steps that can be performed to bleach teeth using a two-part bleaching system.
Figure 5:
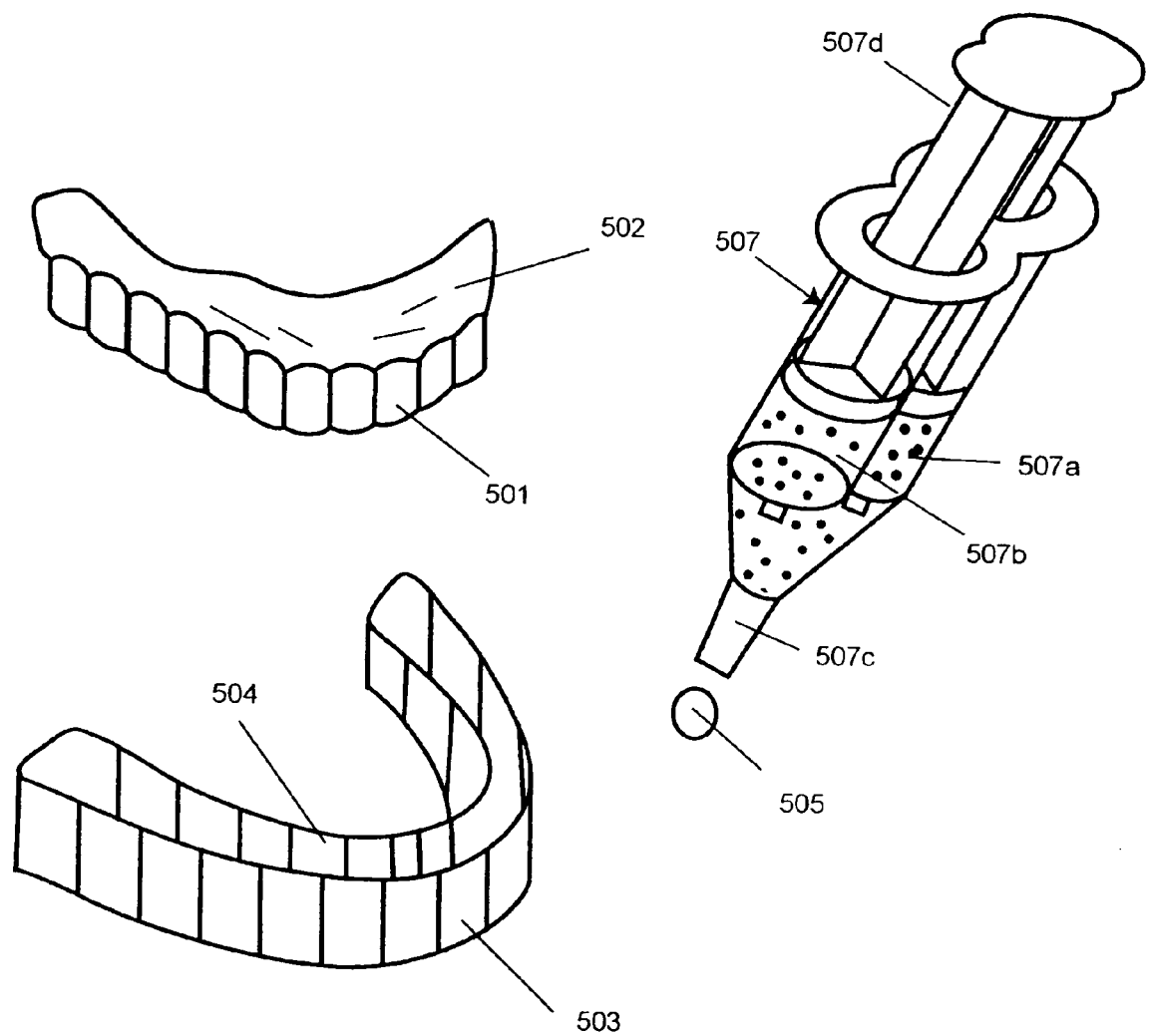
FIG. 5 depicts placing a two-part bleach into a bleaching tray for use in bleaching teeth
Figure 6:
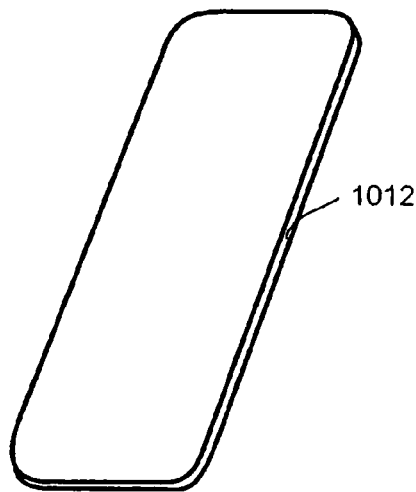
FIG. 6 is a perspective view of a substantially flat strip of material having rounded corners.

In some embodiments, it will be desirable to include a basic substance in the dental bleach. Use of a basic substance can destabilize the bleaching agent such as a peroxide, facilitating release of oxygen ions for dental bleaching. This is particularly desirable if a two-part bleaching system is utilized such as depicted in FIGS. 4 and 5 and as described in their accompanying text. A list of basic substance which may be used in the bleach includes sodium hydroxide, potassium hydroxide, calcium hydroxide and triethanol amine.

5. Flavoring Agent

In some embodiments, it may be desired to add flavorings or sweeteners to the dental bleach. Examples of appropriate sweeteners include aspartame, sodium saccharin, mannitol, fructose, sorbitol, xylitol and the like. Flavorings which may be used include mint, wintergreen, spearmint, berry, lemon, lime, and the like.

6. Desensitizing Agent

Even when they have not been exposed to caustic prior art dental bleaches, some patients experience chronic sensitivity of the teeth and gums. This sensitivity may be alleviated in part by including a desensitizing agent in the dental bleach so that the patient will not experience discomfort or develop apprehension during the bleaching process. Examples of desensitizing agents include fluoride, potassium nitrate, sodium citrate, aloe vera and the like.

7. Other Components

As desired, other components may be included in the bleach as well, including anticariogenic agents and antimicrobial agents which are already known in dentistry.

8. Examples of the Inventive Dental Bleach

The following are some sample compositions of the invented dental bleach. Weight percentages provided indicate the presence of a component as its percentage of the total resulting bleach.

| | | | Exemplary Dental Bleaches | | | |
|---|---|---|---|---|---|---|
| EX. | Bleaching Agent | Thickening Agent | Liquid Component | Basic Substance | Flavoring Agent | Desensitizing Agent |
| 1 | carbamide peroxide about 11% by weight | Polyvinylpyrrolidone 1,000,000 to 1,500,000 molecular weight about 25% by weight | Water about 35% by weight; glycerin about 29% by weight | none | aspartame about 0.5% by weight; peppermint oil about 0.5% by weight | none |

-continued

Exemplary Dental Bleaches

| EX. | Bleaching Agent | Thickening Agent | Liquid Component | Basic Substance | Flavoring Agent | Desensitizing Agent |
|---|---|---|---|---|---|---|
| 2 | carbamide peroxide about 16% by weight | Polyvinylpyrrolidone 1,000,000 to 1,500,000 molecular weight about 30% by weight | Water about 54% by weight | none | None | none |
| 3 | carbamide peroxide about 21% by weight | Polyvinylpyrrolidone 44,000 to 54,000 molecular weight about 30% by weight | glycerine about 49% by weight | none | None | none |
| 4 | carbamide peroxide about 25% by weight | Polyvinylpyrrolidone 1,000,000 to 1,500,000 molecular weight about 30% by weight | Water about 10% by weight; glycerin about 10% by weight | none | None | none |
| 5 | hydrogen peroxide about 3% by weight | Polyvinylpyrrolidone 28,000 to 34,000 molecular weight about 40% by weight | Water about 15% by weight; glycerin about 10%; polyethylene glycol (600 molecular weight) about 42% by weight | none | none | none |
| 6 | hydrogen peroxide about 5% by weight | Polyvinylpyrrolidone 1,000,000 to 1,500,000 molecular weight about 25% by weight | water about 56.39% by weight; polyethylene glycol (600 molecular weight) about 10% by weight | none | none | none |
| 7 | sodium perborate about 25% by weight | Polyvinylpyrrolidone 44,000 to 54,000 molecular weight about 25% by weight | propylene glycol about 50% by weight | none | none | none |
| 8 | sodium perborate about 25% by weight | Polyvinylpyrrolidone 1,000,000 to 1,500,000 molecular weight about 10% by weight; Polyvinylpyrrolidone 44,000 to 54,000 molecular weight about 10% by weight | anhydrous glycerin about 55% by weight | none | none | none |
| 9 | carbamide peroxide about 10.5% by weight | Polyvinylpyrrolidone 100,000 to 150,000 molecular weight about 10% by weight | water about 35.69% by weight; ethanol about 2% by weight; polyethylene glycol (300 molecular weight) about 10% by weight; polyethylene glycol (8000 molecular weight) about 30% by weight | none | aspartame about 0.5% by weight; wintergreen oil about 1% by weight | sodium fluoride about 0.25% by weight; potassium nitrate about 0.1% by weight |
| 10 | carbamide peroxide about 15% by weight | Polyvinylpyrrolidone 1,000,000 to 1,500,000 molecular weight about 25% by weight | water about 20% by weight; anhydrous glycerin about 39.8% by weight | sodium hydroxide about 0.2% by weight | none | none |
| 11 | carbamide peroxide about 25% by weight | Polyvinylpyrrolidone 1,000,000 to 1,500,000 molecular weight about 25% by weight | water about 15% by weight; anhydrous glycerin about 34.8% by weight | sodium hydroxide about 0.2% by weight | none | none |
| 12 | carbamide peroxide about 35% by weight | Polyvinylpyrrolidone 1,000,000 to 1,500,000 molecular weight about 30% by weight | water about 10% by weight; anhydrous glycerin about 24.8% by weight | sodium hydroxide about 0.2% by weight | none | none |
| 13 | carbamide peroxide about 15% by weight | Polyvinylpyrrolidone 1,000,000 to 1,500,000 molecular weight about 35% by weight | water about 15% by weight; anhydrous glycerin about 34.8% by weight | sodium hydroxide about 0.2% by weight | none | none |
| 14 | carbamide peroxide about 15% by weight | Polyvinylpyrrolidone 1,000,000 to 1,500,000 molecular weight about 60% by weight | water about 10% by weight; anhydrous glycerin about 14.8% by weight | sodium hydroxide about 0.2% by weight | none | none |

-continued

Exemplary Dental Bleaches

| EX. | Bleaching Agent | Thickening Agent | Liquid Component | Basic Substance | Flavoring Agent | Desensitizing Agent |
|---|---|---|---|---|---|---|
| 15 | carbamide peroxide about 8% by weight | Polyvinylpyrrolidone 1,000,000 to 1,500,000 molecular weight about 90% by weight | water about 3% by weight; anhydrous glycerin about 4.8% by weight | sodium hydroxide about 0.2% by weight | none | none |
| 16 | carbamide peroxide about 10% by weight | Polyvinylpyrrolidone 1,000,000 to 1,500,000 molecular weight about 85% by weight | water about 2% by weight; anhydrous glycerin about 2.8% by weight | sodium hydroxide about 0.2% by weight | none | none |
| 17 | carbamide peroxide about 31% by weight | Polyvinylpyrrolidone about 23% by weight | Purified water about 30% by weight; anhydrous glycerin about 14.5% by weight | sodium hydroxide about 0.18% by weight | 0.6% peppermint oil; sodium saccharin, about 0.7% by weight | none |
| 18 | carbamide peroxide about 16% by weight | Polyvinylpyrrolidone about 28% by weight | Purified water about 26.1% by weight; anhydrous glycerin about 28.59% by weight | Sodium hydroxide about 0.11% by weight | 0.6% peppermint oil; sodium saccharin, about 0.6% by weight | none |

In some embodiments, percentages of various components can vary as follows:

| Component of Dental Bleach | Broad Range | Typical Range | More Typical Range |
|---|---|---|---|
| Bleaching Agent | 0.1-80% | 0.5-60% | 1-50% |
| Bleaching Agent if Carbamide Peroxide | 0.5-80% | 1-50% | 3-25% |
| Bleaching Agent if Hydrogen Peroxide | 0.1-50% | 0.5-25% | 1-5% |
| Liquid Component | 0.1-99.8% | 0.2-80% | 10-50% |
| Polyvinylpyrrolidone | 0.1-90% | 25-60% | 25-35% |
| Basic Substance | 0-10% | 0.1-9% | 0.2-6% |
| Flavoring Agent | 0-5% | 0.5-3% | 1-2% |

Other ranges of components of dental bleach are possible as well.

The pH ranges of the mixed gel can be as desired, and in many instances may be in the range of 5 to 8, or in the range of 4 to 10. Other pH ranges are possible.

A completed dental bleach of the invention may be a viscous gel that is thick enough that it does not drip out of a syringe of the size typically used in clinical or home dental bleaching where the syringe has a tip aperture that measures from about 2 mm to about 10 mm in diameter. Dental bleaches of other viscosities may be made according to the invention as well.

B. Methods for Performing Dental Bleaching

Figure 2:
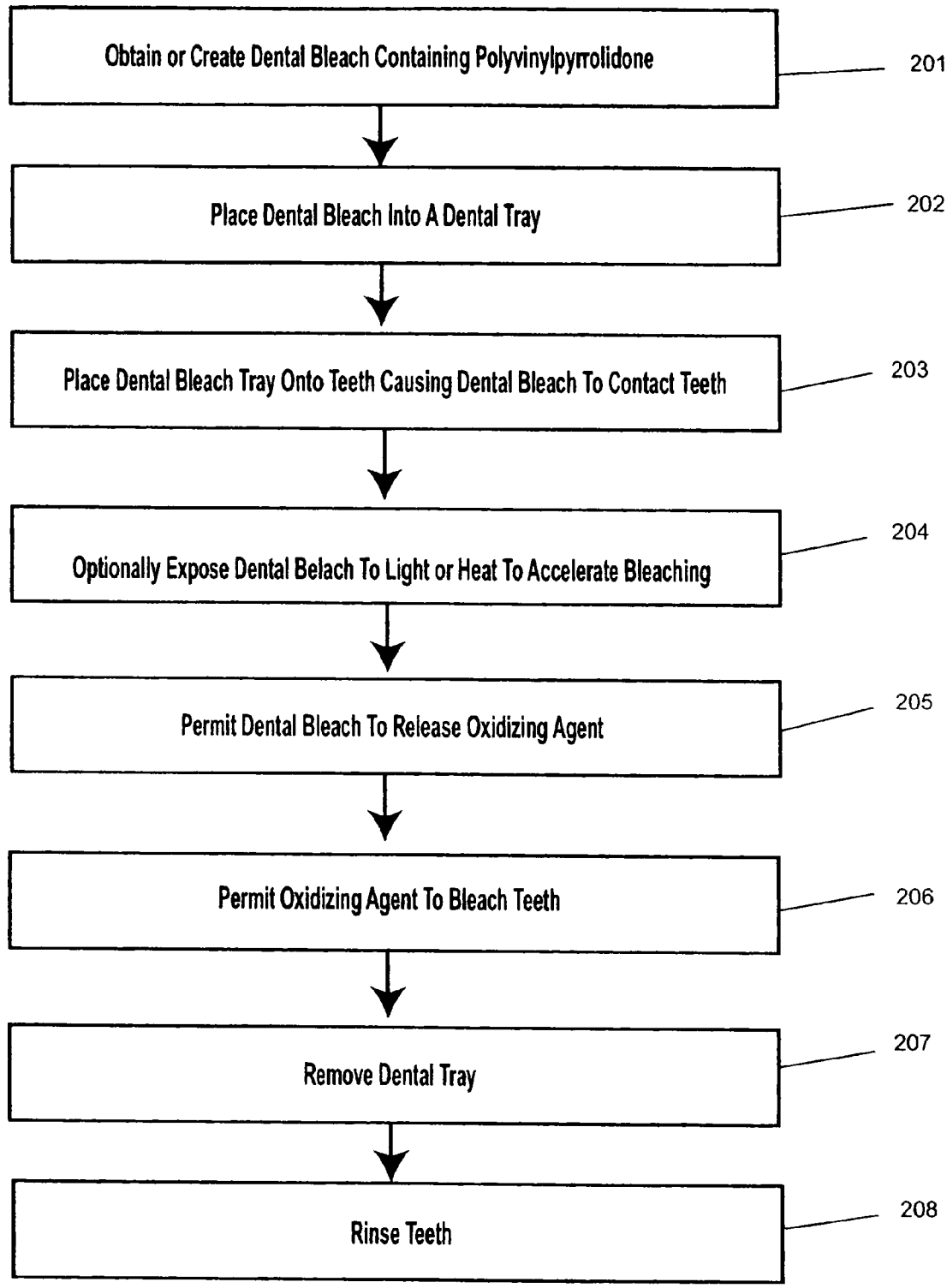
FIG. 2 depicts a series of steps that can be performed to bleach teeth using a one part bleaching system.
Figure 3:
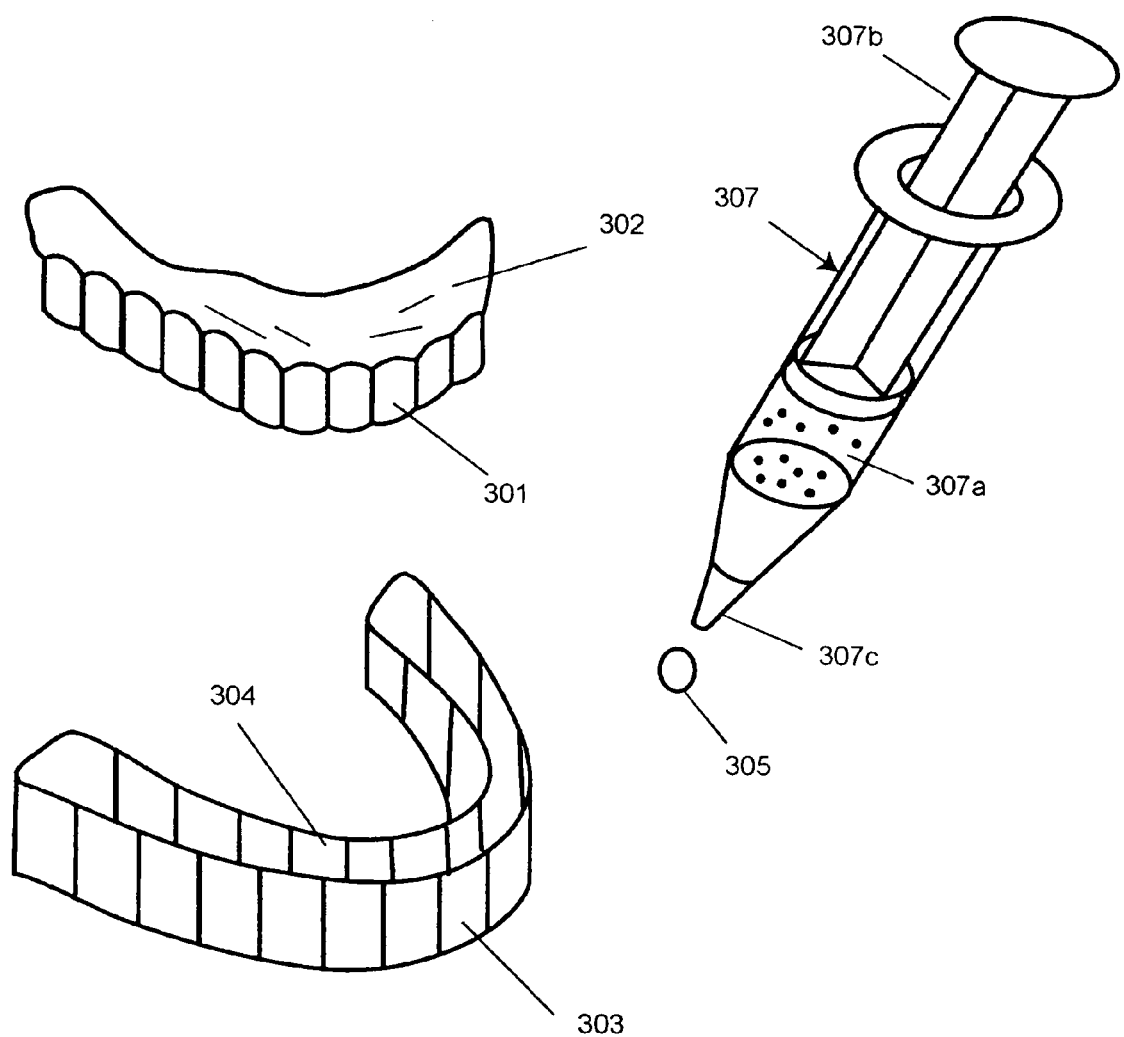
FIG. 3 depicts placing a one-part bleach into a bleaching tray for use in bleaching teeth.

Referring to FIG. 2, a method for performing dental bleaching of a patient's teeth is depicted. First, a dental bleach containing polyvinylpyrrolidone is obtained or created 201 such as by utilizing one of the formulas above. A patient or dental practitioner of patient would likely obtain a dental bleach in a dispenser ready to use as depicted in FIGS. 3 and 5.

Second, the dental bleach is placed into a dental tray 202. The bleach should be spread evenly in the tray and should be of sufficient quantity to cover the exterior surfaces of all teeth. The dental tray may be of a design that does not exert any or much mechanical pressure on a patient's teeth or gums.

Third, the dental tray containing bleach is placed onto the teeth to be bleached, causing the bleach to contact teeth 203. A combination of suction created by placing the tray onto the teeth plus the viscosity of the dental bleach serves to hold the dental tray in place on the teeth during bleaching.

Next, optionally, the dental bleach can be exposed to light or heat in order to accelerate release of its oxidizing agent such as oxygen ions 204. Heat will accelerate any chemical reaction including the reactions of dental bleaching. Some practitioners may use a light to create heat. Some lights that can be used include halogen bulb lights, xenon bulb lights, plasma arc bulb lights, ion gas lasers, semiconductor lasers and light emitting diodes.

Regardless of whether light or heat is used, next, the dental bleach will release an oxidizing agent 205 such as oxidizing ions. The oxidizing agent, when in contact with teeth, will bleach and lighten, whiten or remove stains from the teeth 206. The time that is required for steps 205 and 206 varies, but 1 to 8 hours is common. Shorter and longer times are possible. By utilizing more basic substance or applying heat or a light to the dental bleach, these steps may be accelerated. Alternatively, by using a stronger concentration of bleaching agent, these steps may be accelerated.

Next, the dental tray is removed 207 and the teeth are rinsed 208. This sequence may be performed once in a dental practitioner's office if a strong bleaching agent is used. Or it may be performed several times by a patient in his or her own home. Patients will typically perform the bleaching steps once per day for a couple of weeks, optionally followed by a maintenance regimen.

Referring to FIG. 3, placement of dental bleach 305 into a dental tray 303, and placing the dental tray 303 onto a patient's teeth 301 is depicted. The dental tray 303 has an arch 304 matching the arch of the patient's teeth for containing the dental bleach 305 and keeping it in close contact with the patient's teeth 301 while not placing it against a significant amount of soft tissue 302. If high concentration peroxides are used for bleaching, then a dental dam, rubber protector or fluid light-cured acrylic barrier may be used to keep the dental bleach from contacting soft tissues. Generally, at a concentration of greater than 15% hydrogen peroxide or greater than 40% carbamide peroxide, some type of additional soft tissue protector is desired. The dental tray may be flexible or rigid, and may be made from a suitable material such as plastic or rubber. The tray can be formed in a dental lab to cause it to precisely conform to a patient's teeth, it can be a universal tray such that one size fits all, or it can be a tray that a patient molds himself such as by heating the tray in hot water and then pressing his teeth into it.

A single chamber syringe 307 is provided having a chamber 307a containing dental bleach. A plunger 307b is used to expel a desired quantity of dental bleach 305 from the syringe tip 307c. In some embodiments, the pH of the dental bleach 305 within the syringe will not exceed pH=7, or the bleaching agent may become destabilized prior to use.

Referring to FIG. 4, another method for performing dental bleaching of a patient's teeth is depicted. This method is intended when a two-part dental bleach is utilized. First, a two-part dental bleach containing polyvinylpyrrolidone is obtained or created 401 such as by utilizing one of the formulas above. A patient or dental practitioner of patient would likely obtain a dental bleach in a dispenser ready to use as depicted in FIG. 5. Note that the syringe has two barrels for the two parts of the dental bleach. The components of the two-part dental bleach must be mixed for use 402. Second, the mixed two-part dental bleach is placed into a dental tray 403. Third, the dental tray containing bleach is place onto teeth to be bleached, causing the bleach to contact teeth 404. Next, optionally, the dental bleach can be exposed to light or heat in order to accelerate release of its oxidizing agent such as oxygen ions 405. Regardless of whether light or heat is used, next, the dental bleach will release an oxidizing agent 406 such as oxygen ions. The oxidizing agent, when in contact with teeth, will bleach and lighten, whiten or remove stains from the teeth 407. Next, the dental tray is removed 408 and the teeth are rinsed 409.

Referring to FIG. 5, use of a dental bleach dispenser 507 such as a double barrel syringe is depicted. The double barrel syringe 507 has a first chamber 507a and a second chamber 507b. Both chambers may be of equal volume for ease of determining the final mixture of the dental bleach, although double barrel syringes with two chambers of unequal volumes can be used as well. Likewise, multi-chamber syringes may be used for multi-component bleaches. The two chambers 507a and 507b may also contain gels of approximately equal viscosities for ease and efficiency of mixing. The first chamber 507a may contain an oxidizing agent such as a peroxide in a concentration such that when the two components of the bleach are mixed from the two chambers, the resulting bleach 505 has the desired concentration of bleaching agent. The chamber 507a containing the bleaching agent 507a may have a pH=7 or less for stability of the bleaching agent. The contents of the second chamber 507b will include a basic substance and will have a pH in the range of about 7 to 12. However, the second chamber 507b will typically not include a bleaching agent. The remainder of the components of the dental bleach may be equally present in both chambers of the syringe, although other pre-dispensing mixes are possible.

As the plunger 507d of the dental bleach dispenser 507 is depressed, the contents of the first chamber 507a and the second chamber 507b are forced through a mixing tip 507c where they are mixed. This mixing contacts the basic substance with the bleaching agent. As the basic substance will tend to destabilize the bleaching agent, the bleaching agent will generate oxygen radicals more rapidly. The pH of the resulting mixed dental bleach 505 may be greater than the pH of the dental bleach dispensed from the syringe of FIG. 3.

The mixed bleach 505 is placed into the arch 504 of a dental tray 503, and the dental tray 503 is placed over teeth 501. The bleach 505 with destabilized bleaching agent will release large quantities of oxidizing agent quickly to perform rapid and thorough bleaching of the teeth 501. The dental tray 503 serves to retain the bleach 505 on the teeth 501 and to keep the bleach 505 away from most soft tissue 502.

Referring now to the drawings, and more particularly to FIGS. 11 and 12, there is shown a device which is generally indicated as 1010. Embodiment 1010 represents a delivery system for a tooth whitening substance. Delivery system 1010 has a strip of material 1012, which may be initially substantially flat with rounded corners.

Figure 8:
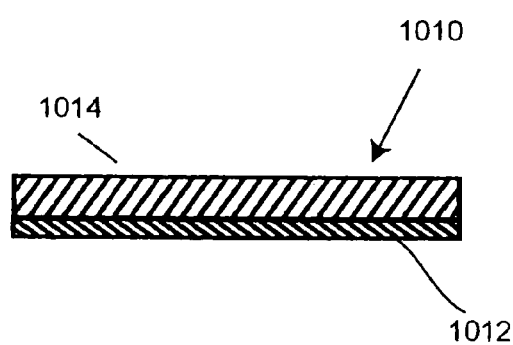
FIG. 8 is a cross-sectional view thereof, taken along section line 8-8 of FIG. 7, disclosing an example of the flat strip having a thickness less than that of the substance coated thereon.

Applied or coated onto strip of material 1012, or embedded into the strip of material 1012 if the material is porous, is a tooth whitening substance 1014. Substance 1014 maybe homogeneous, uniformly and continuously coated onto strip of material 1012, as shown in FIG. 8, or embedded into the strip of material if the material is porous. However, substance 1014 may alternatively be a laminate or separated layers of components, an amorphous mixture of components, separate stripes or spots or other patterns of different components, or a combination of these structures, including a continuous coating of oral care substance 1014 along a longitudinal axis of a portion of strip of material 1012.

Figure 9:
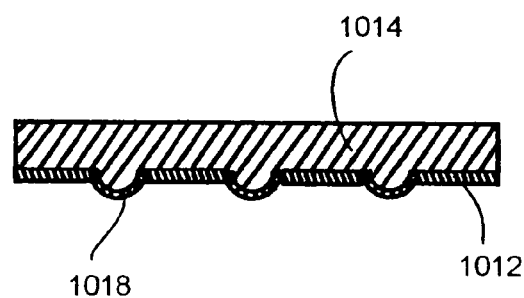
FIG. 9 is a cross-sectional view showing another bleaching system, showing shallow pockets in the strip of material, which act as reservoirs for additional substance coated on the strip.

As shown in FIG. 9, an alternative embodiment, a strip of material 1012 may have shallow pockets 1018 formed therein. When substance 1014 is coated on a substance-coated side of strip of material 1012, additional substance 1014 fills shallow pockets 1018 to provide reservoirs of additional substance 1014.

FIGS. 10 and 11 show a delivery system 1024 applied to a plurality of adjacent teeth and the surface of a tooth. Embedded in adjacent soft tissue 1020 is a plurality of adjacent teeth 1022. Adjacent soft tissue is herein defined as soft tissue surfaces surrounding the tooth structure including: papilla, marginal gingiva, gingival sulcus, inter dental gingiva, gingival gum structure on lingual and buccal surfaces up to and including muco-gingival junction and the pallet.

In both FIGS. 10 and 11, delivery system 1024 represents strip of material 1012 and substance 1014, with substance 1014 on the side of strip of material 1012 facing adjacent teeth 1022. Substance 1014 may be pre-applied to strip of material 1012 or applied to strip of material 1012 by the delivery system user. In either case, strip of material 1012 has a thickness and flexural stiffness which enable it to conform to the contoured surfaces of adjacent teeth 1022 and to adjacent soft tissue 1020. The strip of flexible material has sufficient flexibility to form a curved shape around a plurality of adjacent teeth. The strip of material is also readily conformable to tooth surfaces and to the interstitial tooth spaces without permanent deformation when the delivery system is applied. The delivery system is applied without significant pressure.

FIGS. 12 and 13 show delivery system 1024 applied to both front and rear surfaces of a plurality of adjacent teeth 1022 as well as to adjacent soft tissue 1020 located by the front surfaces of the teeth. Delivery system 1024 represents strip of material 1012 and substance 1014, with substance 1014 on the side of strip of material 1012 facing adjacent teeth.

Figure 14:
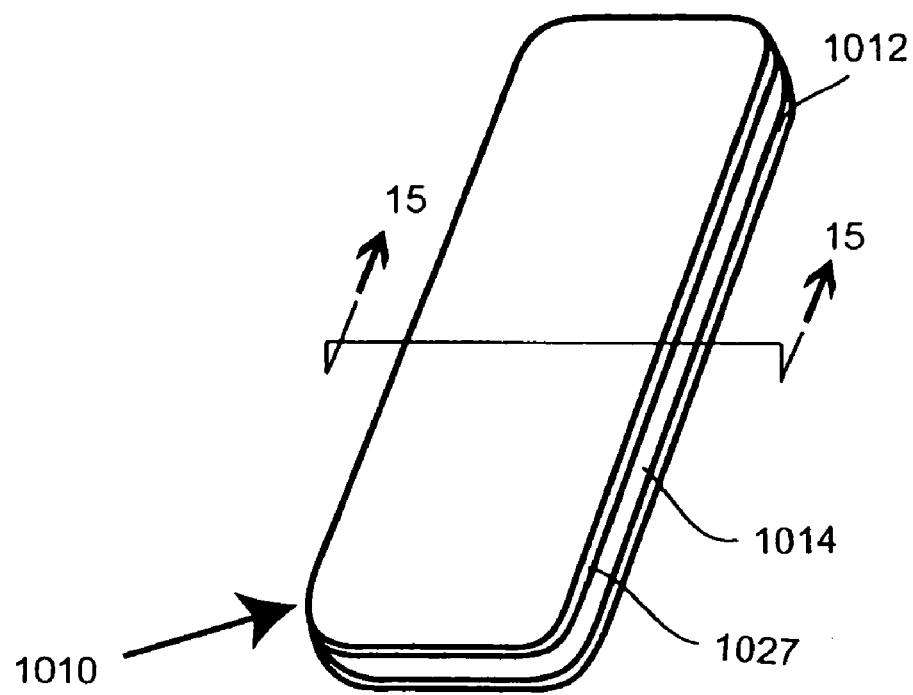
FIG. 14 is a perspective view of a bleaching system disclosing the flat strip coated with a tooth whitening substance of FIG. 7 with a release liner.
Figure 15:
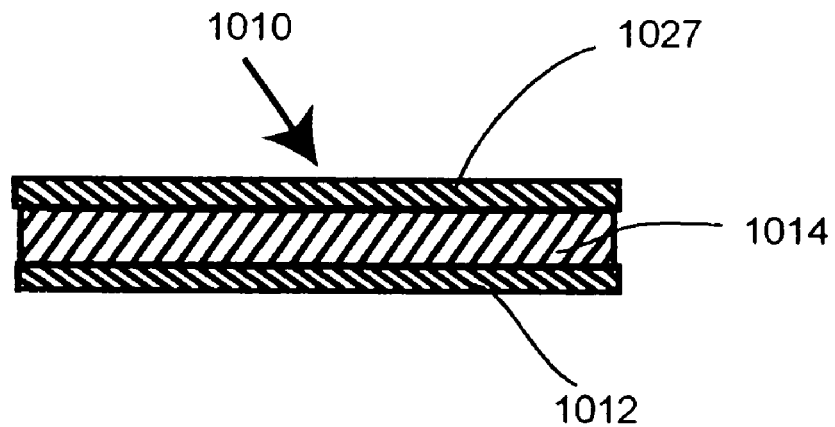
FIG. 15 is a cross-section view taken along section line 15-15 of FIG. 14, showing a release liner attached to the strip of material by the substance on the strip of material.

FIGS. 14 and 15 shows an optional release liner 1027. Release liner 1027 is attached to strip of material 1012 by substance 1014. Substance 1014 is on the side of strip of material 1012 facing release liner 1027. This side is applied to the tooth surface once release liner 1027 is removed.

The strip of material serves as a protective barrier to substantially prevent saliva contacting the tooth whitening substance and leaching and/or erosion of the tooth whitening substance from the surface of the teeth by the wearer's lips, tongue, and other soft tissue. In order for an active in tooth whitening substance to act upon the surface of tooth over an extended period of time, from several minutes to several hours, it is important to minimize such leaching and/or erosion. The term "act upon" is herein defined as bringing about a desired change. For example, if the substance is a tooth whitener, it bleaches color bodies to bring about whitening.

The strip of material may comprise materials such as polymers, natural and synthetic wovens, non-wovens, foil, paper, rubber, and combinations thereof. The strip of material may be a single layer of material or a laminate of more than one layer. Generally, the strip of material is substantially water impermeable. The material may be any type of polymer that meets the required flexural rigidity and is compatible with tooth whitening actives, such as peroxide. The material may comprise a single polymer or a mixture of polymers. Suitable polymers include, but are not limited to, polyethylene, ethylvinylacetate, ethylvinyl alcohol, polyesters such as Mylar® manufactured by DuPont, fluoroplastics such as Teflon® manufactured by DuPont, and combinations thereof. The material may be polyethylene. The strip of material is generally less than about 1 mm thick, or less than about 0.05 mm thick, or from about 0.001 to about 0.03 mm thick. A polyethylene strip of material may be less than about 0.1 mm thick or from about 0.005 to about 0.02 mm thick.

The shape of the strip of material may be any shape that has rounded corners. "Rounded corners" is defined as not having any sharp angles or points. The conformable strip of material may be of a size that individually fits the row of teeth desired to be bleached. Generally, this is the front 6-8 teeth of the upper or lower rows of teeth that are visible when the wearer is smiling. Optionally, the strip of material may fit the entire upper or lower rows of teeth when positioned against the teeth. The size of the strip of material depends upon many factors, including the number of teeth to be bleached, the size of the teeth, and personal preference of the wearer. In general, the length of the strip of material is from about 2 cm to about 12 cm, or from about 4 cm to about 9 cm. The width of the strip of material will also depend upon many factors, including whether or not the strip of material wraps around the teeth and covers both surfaces of the tooth. In a general application, the width of the strip of material is from about 0.5 cm to about 4 cm, or from about 1 to about 2 cm.

The strip of material may contain shallow pockets. When the substance is coated on a substance-coated side of strip of material, additional substance fills shallow pockets to provide reservoirs of additional substance. Additionally, the shallow pockets help to provide a texture to the delivery system. The film may have an array of shallow pockets. Generally, the shallow pockets are approximately 0.4 mm across and 0.1 mm deep. When shallow pockets are included in the strip of material and substances are applied to it in various thicknesses, the overall thickness of the delivery system is generally less than about 1 mm. The overall thickness may be less than about 0.5 mm.

Flexural stiffness is a material property that is a function of a combination of strip thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A micrometer, wired to the strain gauge, is calibrated in grams of deflection force. The rigidity of the sample is read directly from the microammeter and expressed as grams per centimeter of sample strip width. In some embodiments, the strip of material has a flexural stiffness of less than about 5 grams/cm as measured on a Handle-O-Meter, model #211-300, available from Thwing-Albert Instrument Co. of Philadelphia, Pa., as per test method ASTM D2923-95. The strip of material may have a flexural stiffness less than about 4 grams/cm, or less than about 3 grams/cm, or from about 0.1 grams/cm to about 1 grams/cm. The flexural stiffness of the strip of material may be substantially constant and not significantly change during normal use. For example, the strip of material does not need to be hydrated for the strip to achieve the low flexural stiffness in the above-specified ranges.

This relatively low stiffness enables the strip of material to drape over the contoured surfaces of teeth with very little force being exerted; that is, conformity to the curvature of the wearer's mouth and gaps between adjacent teeth is maintained because there is little residual force within strip of material to cause it to return to its substantially flat shape. The flexibility of the strip enables the strip of material to contact adjoining soft tissue over an extended period of time without physical irritation. The strip of material does not require pressure forming it against the teeth.

The strip of material is held in place on a plurality of adjacent teeth by adhesive attachment provided by the substance. The viscosity and general tackiness of the substance cause the strip of material to be adhesively attached to a plurality of adjacent teeth without substantial slippage under the potential friction from the lips, tongue, and other soft tissue rubbing against the strip of material during mouth movements associated with talking, drinking, etc. However, this adhesion to the teeth is low enough to allow the delivery system to be easily removed by the wearer by peeling off the strip of material using one's finger or fingernail. The delivery system is easily removable from the surfaces of the teeth without the use of an instrument, a chemical solvent, or undue friction. Chemical solvents include any organic solvents commonly used in oral care products such as alcohol and other safe solvents such as water, which could be used to dilute the gelling agent. Undue friction is described as any type of rubbing with one's finger or a soft implement, such as cotton balls, swabs, or gauze pads.

A peel force of from about 1 gram to about 50 grams for a 1.5 cm strip width (approximately 17 grams/cm) is all that is required. The peel force may be from about 5 grams to about 40 grams, or from about 10 grams to about 30 grams. The low peel force is desired for consumer handling purposes. The low peel force is possible because of the non-aggressive nature of a gel substance. Only when the flexural stiffness of the strip is low can the adhesion of the substance also be low. The adhesion of a stiffer strip would have to be greater in proportion to the strip stiffness in order to prevent the strip from returning to its flat condition and pulling away from the contoured surface of a plurality of teeth.

The strip of material may be formed by several of the film making processes known in the art. A strip of material made of polyethylene may be made by a blowing process or a cast process. Processes, such as extrusion and other processes that do not affect the flexural rigidity of the strip of material, are also feasible. Additionally, the substance may be incorporated onto the strip during the processing of the strip. The substance may be a laminate on the strip.

While the present embodiments have been described and illustrated in conjunction with a number of specific embodiments, those skilled in the art will appreciate that variations and modifications may be made without departing from the principles as herein illustrated, described and claimed. The devices may be embodied in other specific forms without departing from their spirit or characteristics. The described embodiments are to be considered in all respects as only illustrative, and not restrictive. The scope of the invention is, therefore, indicated by the appended claims, rather than the foregoing description. All changes that come within the meaning and range of equivalency of the claims are to be embraced within their scope.

What is claimed is:

1. A kit for bleaching teeth comprising:
    a dental tray; and
    a stable one-part dental bleaching composition that is safe for use in an oral cavity of a person's mouth over a time period of at least 1 hour and that is sticky and viscous so as to adhere the dental tray adjacent to a person's teeth during dental bleaching, the dental bleaching composition comprising:
        a dental bleaching agent selected from the group comprising hydrogen peroxide, carbamide peroxide, sodium perborate, and sodium percarbonate and included in an amount in a range of 1% to 50% by weight of the dental bleaching composition;
        a liquid carrier component comprising water in an amount of at least 0.1% by weight of the dental bleaching composition and at least one polyol; and
        polyvinylpyrrolidone having a molecular weight in a range of 1,000,000 to 1,500,000 and included in an amount of 5-40% by weight of the dental bleaching composition so as to form a sticky, viscous aqueous gel when mixed with the liquid carrier component and dental bleaching agent, wherein the polyvinylpyrrolidone promotes adhesion of the dental bleaching composition to tooth enamel without the polyvinylpyrrolidone removing calcium from tooth enamel by chelation,
        wherein the dental bleaching composition, when used to adhere the dental tray to a person's teeth, has an adhesiveness so as to hold the dental tray against the person's teeth without substantial slippage.

2. A kit as recited in claim 1, said water having a concentration of at least 0.2% by weight of the dental bleaching composition.

3. A kit as recited in claim 1, said water having a concentration of 10-50% by weight of the dental bleaching composition.

4. A kit as recited in claim 1, said liquid carrier component comprising at least one component selected from the group comprising glycerin, propylene glycol, liquid polyethylene glycol, liquid polypropylene glycol, and ethanol.

5. A kit as recited in claim 1, said liquid carrier component is present in an amount of at least 0.2% of the dental bleaching composition.

6. A kit as recited in claim 1, said liquid carrier component is present in an amount of 10-50% by weight of the dental bleaching composition.

7. A kit as recited in claim 1, the dental bleaching composition further comprising at least one thickening agent selected from the group comprising fumed silica, xanthan gum, pectin, guar gum, hydroxyl propyl cellulose, gelatin, natural gums, polyethylene glycol, polypropylene glycol, carboxypolymethylene, and water soluble waxes.

8. A kit as recited in claim 1, wherein said polyvinylpyrrolidone is the sole or primary tooth adhesion agent.

9. A kit as recited in claim 1, further comprising a base to raise the pH of the dental bleaching composition.

10. A kit as recited in claim 1, further comprising a tooth desensitizing agent.

11. A kit as recited in claim 10, wherein said tooth desensitizing agent is selected from the group consisting of potassium nitrate, sodium citrate and aloe vera.

12. A kit for bleaching teeth, comprising:
    at least one barrier layer comprising a flexible strip of material; and
    a one-part dental bleaching composition that is safe for use in an oral cavity of a person's mouth over a time period of at least 1 hour and that is adhesive so as to adhere the strip of material adjacent to a person's teeth during dental bleaching, the dental bleaching composition comprising:
        a dental bleaching agent selected from the group comprising hydrogen peroxide, carbamide peroxide, sodium perborate, and sodium percarbonate and included in an amount in a range of 1% to 50% by weight of the dental bleaching composition;
        water in an amount of at least 0.1% by weight of the dental bleaching composition; and
        polyvinylpyrrolidone having a molecular weight in a range of 1,000,000 to 1,500,000, wherein the polyvinylpyrrolidone promotes adhesion of the dental bleaching composition to tooth enamel without the polyvinylpyrrolidone removing calcium from tooth enamel by chelation,
        wherein the dental bleaching composition, when used to adhere a dental tray or strip of material to a person's teeth, has an adhesiveness so as to hold the strip of material against the person's teeth without substantial slippage.

13. A kit for bleaching teeth, comprising:
    at least one barrier layer comprising a flexible strip of material; and
    a dental bleaching composition that is safe for use in an oral cavity of a person's mouth over a time period of at least 1 hour and that is adhesive so as to adhere the strip of material adjacent to a person's teeth during dental bleaching, the dental bleaching composition comprising:
        a dental bleaching agent included in an amount in a range of 1% to 50% by weight of the dental bleaching composition;
        water in an amount of at least 0.1% by weight of the dental bleaching composition; and
        at least one tooth adhesion agent in an amount of at least 25% by weight of the dental bleaching composition, the tooth adhesion agent comprising polyvinylpyrrolidone having a molecular weight in a range of 1,000,000 to 1,500,000, wherein the tooth adhesion agent promotes adhesion of the dental bleaching composition to tooth enamel without the polyvinylpyrrolidone removing calcium from tooth enamel by chelation,
        wherein the dental bleaching composition, when used to adhere a dental tray or strip of material to a person's teeth, has an adhesiveness so as to hold the strip of material against the person's teeth without substantial slippage.

14. A stable one part dental bleaching composition that is safe for use in an oral cavity of a person's mouth over a time period of at least 1 hour and that is sticky and viscous so as to adhere a barrier layer adjacent to a person's teeth during dental bleaching, the dental bleaching composition comprising:
  a dental bleaching agent selected from the group comprising hydrogen peroxide, carbamide peroxide, sodium perborate, and sodium percarbonate and included in an amount in a range of 1% to 50% by weight of the dental bleaching composition;
  water in a concentration of less than 50% by weight of the dental bleaching composition;
  a polyol; and
  at least one tooth adhesion agent in a concentration of about 25% or greater by weight of the dental bleaching composition that, when mixed with the dental bleaching agent, water and polyol, forms a sticky, viscous aqueous gel, the tooth adhesion agent comprising polyvinylpyrrolidone having a molecular weight in a range of 1,000,000 to 1,500,000, wherein the tooth adhesion agent promotes adhesion of the dental bleaching composition to tooth enamel without the polyvinylpyrrolidone removing calcium from tooth enamel by chelation,
  wherein the dental bleaching composition, when used to adhere a dental tray or strip of material to a person's teeth, has an adhesiveness so as to hold the dental tray or strip of material against the person's teeth without substantial slippage.

15. A kit for bleaching teeth comprising the dental bleaching composition recited in claim 14 and at least one barrier layer.

16. A dental bleaching composition as in claim 14, wherein the dental bleaching agent comprises at least one member selected from the group consisting of carbamide peroxide, sodium perborate, and sodium percarbonate.

17. A dental bleaching composition as in claim 14, further comprising silica.

18. A dental bleaching composition as in claim 14, further comprising a flavoring agent.

19. A dental bleaching system comprising a barrier layer in contact with a dental bleaching composition as in any of claims 14-18.

20. A kit as defined in any of claim 1, 15, 12 or 13, the dental bleaching composition being preloaded within a syringe.

21. A kit as defined in claim 15, said barrier layer comprising a flexible strip of material.

22. A kit as defined in claim 15, said barrier layer comprising a dental tray.

23. A stable one part dental bleaching composition that is safe for use in an oral cavity of a person's mouth over a time period of at least 1 hour and that is adhesive so as to adhere a dental tray or strip of material adjacent to a person's teeth during dental bleaching, the dental bleaching composition comprising:
  a dental bleaching agent selected from the group comprising hydrogen peroxide, carbamide peroxide, sodium perborate, and sodium percarbonate and included in an amount in a range of 1% to 50% by weight of the dental bleaching composition;
  water in a concentration of 0.1% to 50% by weight of the dental bleaching composition;
  a polyol;
  a flavoring agent; and
  polyvinylpyrrolidone having a molecular weight in a range of 1,000,000 to 1,500,000 and optionally at least one other tooth adhesion agent having a total concentration of at least 25% by weight of the dental bleaching composition so that, in combination with the dental bleaching agent, water, and polyol, forms a composition that is adhesive to teeth, wherein the polyvinylpyrrolidone promotes adhesion of the dental bleaching composition to tooth enamel without removing calcium from tooth enamel,
  wherein the dental bleaching composition, when used to adhere a dental tray or strip of material to a person's teeth, has an adhesiveness so as to hold the dental tray or strip of material against the person's teeth without substantial slippage.

24. A dental bleaching composition as in claim 23, wherein the flavoring agent comprises at least one of aspartame, sodium saccharin, mannitol, fructose, sorbitol, or xylitol.

25. A dental bleaching composition as in claim 23, further comprising silica.

26. A dental bleaching composition as in any of claims 23-25, wherein the dental bleaching composition comprises a thin strip.

27. A stable one-part dental bleaching composition that is safe for use in an oral cavity of a person's mouth over a time period of at least 1 hour and that is sticky and viscous so as to adhere the dental tray adjacent to a person's teeth during dental bleaching, the dental bleaching composition comprising:
  a dental bleaching agent selected from the group comprising hydrogen peroxide, carbamide peroxide, sodium perborate, and sodium percarbonate and included in an amount in a range of 1% to 50% by weight of the dental bleaching composition;
  water in a concentration of 0.1% to 50% by weight of the dental bleaching composition;
  a polyol; and
  polyvinylpyrrolidone having a molecular weight in a range of 1,000,000 to 1,500,000 and included in an amount so as to form a sticky, viscous aqueous gel when mixed with the liquid carrier component and dental bleaching agent, wherein the polyvinylpyrrolidone promotes adhesion of the dental bleaching composition to tooth enamel without the polyvinylpyrrolidone removing calcium from tooth enamel by chelation,
  wherein the dental bleaching composition, when used to adhere a dental tray or strip of material to a person's teeth, has an adhesiveness so as to hold the dental tray or strip of material against the person's teeth without substantial slippage.

* * * * *

UNITED STATES PATENT AND TRADEMARK OFFICE
CERTIFICATE OF CORRECTION

Page 1 of 2

PATENT NO. : 7,862,801 B2
APPLICATION NO. : 10/870293
DATED : January 4, 2011
INVENTOR(S) : Chen It is certified that error appears in the above-identified patent and that said Letters Patent is hereby corrected as shown below:

Drawings
Sheet 2, replace Figure 2 with the figure depicted below, wherein in step 204, "Belach" has been changed to --Bleach--

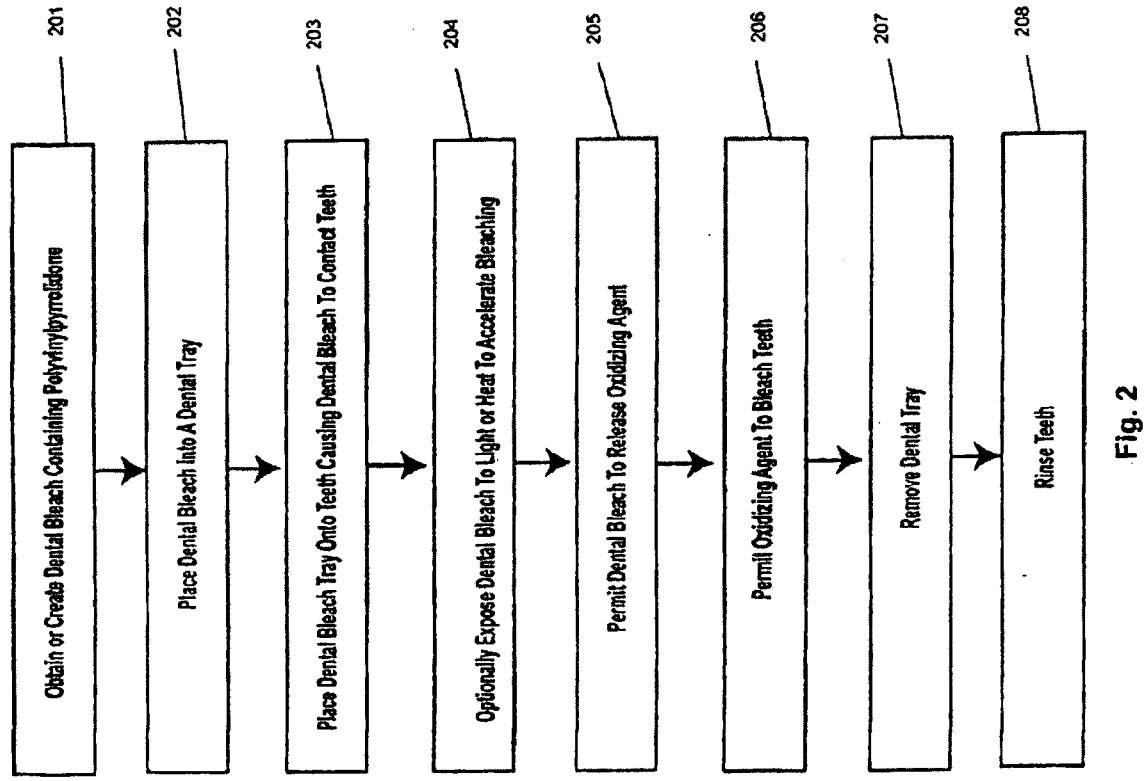

Column 4
Line 41, change "regimes" to --regimens--

Column 5
Line 22, change "ionoic" to --ionic--

Signed and Sealed this
Third Day of May, 2011

David J. Kappos
*Director of the United States Patent and Trademark Office*

CERTIFICATE OF CORRECTION (continued)
U.S. Pat. No. 7,862,801 B2

Column 6
Line 37, change "teeth" to --teeth.--

Column 8
Line 27, change "substance" to --substances--

Column 11
Line 62, change "of patient" to --of a patient--

Column 13
Line 28, change "place" to --placed--

Figure 7:
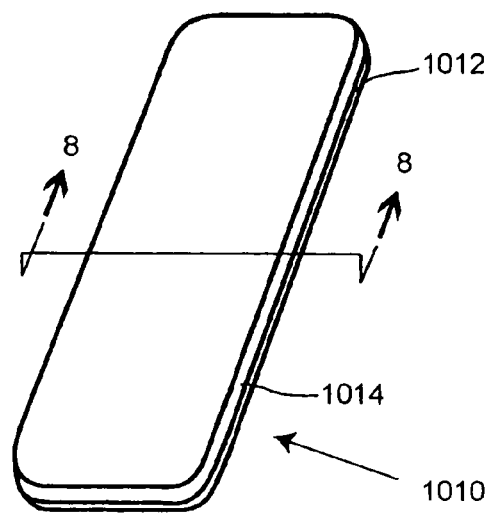
FIG. 7 is a perspective view of a bleaching system, disclosing the flat strip of FIG. 6 coated with a tooth whitening substance.

Column 14
Line 11, change "FIGS. 11 and 12" to --FIGS. 7 and 8--
Line 18, change "maybe" to --may be--
Line 63, change "shows" to --show--

Column 19
Line 9, change "less than" to --0.1% to--